United States Patent
Chen et al.

(10) Patent No.: US 10,132,958 B2
(45) Date of Patent: Nov. 20, 2018

(54) DETERMINING AN OPTICAL DENSITY LINEAR DYNAMIC RANGE FOR AN OPTICAL SPECTROMETER

(71) Applicant: Schlumberger Technology Corporation, Sugar Land, TX (US)

(72) Inventors: Yuehua Chen, Machida (JP); Cong Wang, Sagamihara (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 101 days.

(21) Appl. No.: 15/209,839

(22) Filed: Jul. 14, 2016

(65) Prior Publication Data
US 2018/0017705 A1    Jan. 18, 2018

(51) Int. Cl.
| | |
|---|---|
| G01V 8/00 | (2006.01) |
| G01N 21/25 | (2006.01) |
| G01N 21/27 | (2006.01) |
| G01N 21/3577 | (2014.01) |

(52) U.S. Cl.
CPC ............... *G01V 8/00* (2013.01); *G01N 21/25* (2013.01); *G01N 21/274* (2013.01); *G01N 21/3577* (2013.01)

(58) Field of Classification Search
CPC .................................. G01N 21/25; G01V 8/00
See application file for complete search history.

(56) References Cited

U.S. PATENT DOCUMENTS

| | | | | |
|---|---|---|---|---|
| 4,832,488 A | * | 5/1989 | Hirai | G01N 33/52 356/243.2 |
| 5,161,409 A | * | 11/1992 | Hughes | E21B 21/08 250/255 |
| 5,260,574 A | * | 11/1993 | Becker | G01J 1/24 250/338.1 |
| 5,521,269 A | * | 5/1996 | Miyashita | C07D 491/10 526/259 |
| 5,592,290 A | * | 1/1997 | Arai | G01N 21/274 356/243.5 |
| 6,474,152 B1 | * | 11/2002 | Mullins | G01N 21/359 166/250.01 |
| 7,095,012 B2 | * | 8/2006 | Fujisawa | E21B 47/102 250/255 |

(Continued)

FOREIGN PATENT DOCUMENTS

WO     WO2014003840 A1    1/2014

OTHER PUBLICATIONS

International Search Report and Written Opinion issued in International Patent application PCT/PCT/US2017/042027 dated Oct. 24, 2017. 11 pages.

*Primary Examiner* — David Porta
*Assistant Examiner* — Djura Malevic (57) ABSTRACT

A technique includes acquiring dry condition and wet measurements using an optical spectrometer for a plurality of lamp intensities. The technique includes determining candidate maximum optical densities as a function of the lamp intensities based at least in part on a reference measurement that is acquired by the spectrometer, the reference measurement and does not vary with respect to the lamp intensities. The technique includes determining an optical density linear dynamic range based at least in part on the candidate maximum optical densities.

20 Claims, 7 Drawing Sheets

(56) References Cited

U.S. PATENT DOCUMENTS

| | | | | |
|---|---|---|---|---|
| 7,361,472 B2* | 4/2008 | Yguerabide | ......... | C12Q 1/6816 |
| | | | | 356/300 |
| 7,758,812 B2* | 7/2010 | Pachl | ................ | G01N 21/8483 |
| | | | | 422/82.05 |
| 8,020,437 B2* | 9/2011 | Zhan | ....................... | E21B 49/08 |
| | | | | 73/152.22 |
| 8,445,841 B2* | 5/2013 | Szobota | ............... | G01N 21/552 |
| | | | | 250/254 |
| 2004/0069942 A1* | 4/2004 | Fujisawa | .............. | E21B 47/102 |
| | | | | 250/269.1 |
| 2008/0087078 A1* | 4/2008 | Vannuffelen | .......... | E21B 47/102 |
| | | | | 73/152.54 |
| 2008/0259318 A1* | 10/2008 | Pan | .......................... | G01J 3/02 |
| | | | | 356/73 |
| 2011/0108719 A1* | 5/2011 | Ford | ........................ | G01J 3/02 |
| | | | | 250/262 |
| 2012/0309636 A1* | 12/2012 | Gibbons | ............... | B01L 3/0275 |
| | | | | 506/9 |
| 2013/0009048 A1* | 1/2013 | Xie | ....................... | G01N 21/33 |
| | | | | 250/256 |
| 2014/0293282 A1 | 10/2014 | Indo et al. | | |
| 2016/0006928 A1* | 1/2016 | Gibbons | ............... | B01L 3/0275 |
| | | | | 348/79 |
| 2016/0178435 A1 | 6/2016 | Indo et al. | | |
| 2017/0077429 A1* | 3/2017 | Huang | ................ | H01L 51/426 |

\* cited by examiner

DETERMINING AN OPTICAL DENSITY LINEAR DYNAMIC RANGE FOR AN OPTICAL SPECTROMETER

BACKGROUND

The following descriptions and examples are not admitted to be prior art by virtue of their inclusion in this section.

A downhole tool may be deployed in a wellbore that traverses a hydrocarbon bearing geologic structure for purposes of acquiring information about fluids of the geologic structure. For this purpose, the downhole tool may contain an optical spectrometer. The optical spectrometer measures how a downhole fluid interacts with light for purposes of determining information about the fluid.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with an example implementation, a technique includes acquiring dry condition and wet condition measurements using an optical spectrometer for a plurality of lamp intensities. The technique includes determining candidate maximum optical densities as a function of the lamp intensities based at least in part on a reference measurement that is acquired by the spectrometer. The reference measurement does not vary with respect to the lamp intensities. The technique includes determining an optical density linear dynamic range based at least in part on the candidate maximum optical densities.

In accordance with another example implementation, a technique includes acquiring a plurality of wet condition measurements using an optical spectrometer for a range of values for a lamp current of the spectrometer; and acquiring a plurality of dry condition measurements using the spectrometer for the range of values for the lamp current. The technique further includes determining first measurement-to-reference ratios for the wet condition measurements; and determining second measurement-to-reference ratios for the dry condition measurements. The technique also includes acquiring a fixed, reference attenuation measurement by the spectrometer; and determining candidate maximum optical densities for the spectrometer for the lamp current values based at least in part on the wet and dry condition measurements and the reference measurement. The technique still further includes determining an optical density linear dynamic range based at least in part on the candidate maximum optical densities and errors of the candidate optical densities with respect to a reference maximum optical density.

In accordance with yet another example implementation, an apparatus includes an interface and a processor. The interface receives data representing net intensities that are measured by an optical spectrometer performing wet condition and dry condition measurements for a plurality of lamp currents. The processor processes the data to determine the candidate maximum optical densities for the lamp current intensities based at least in part on a reference measurement acquired by the spectrometer. The reference measurement does not vary with respect to the lamp current. The processor processes the data to determine an optical density linear dynamic range based at least in part on the candidate maximum optical densities and a reference maximum optical density.

Advantages and other features will become apparent from the following drawings, description and claims.

BRIEF DESCRIPTION OF THE DRAWINGS

Certain embodiments will hereafter be described with reference to the accompanying drawings, wherein like reference numerals denote like elements. It should be understood, however, that the accompanying drawings illustrate only the various implementations described herein and are not meant to limit the scope of various technologies described herein. The drawings are as follows.

DETAILED DESCRIPTION

Figure 1:
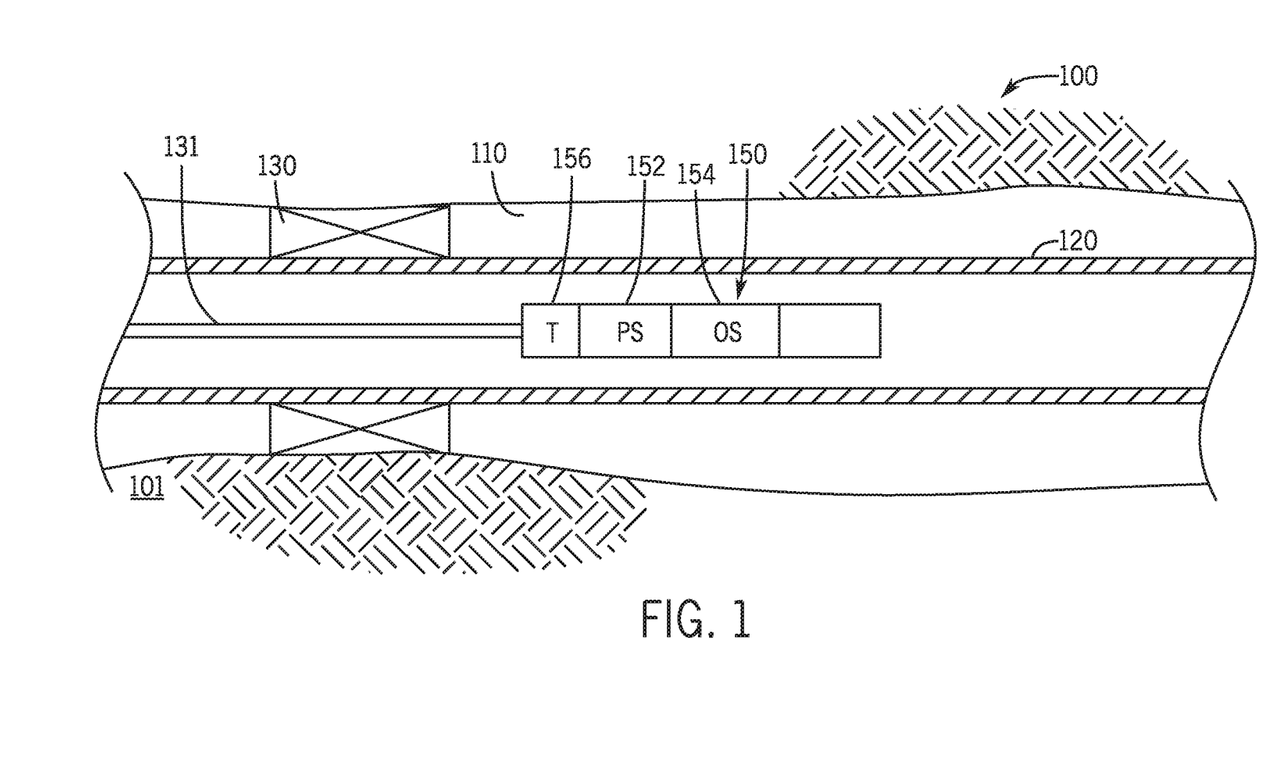
FIG. 1 is a schematic diagram of a well according to an example implementation.

Referring to FIG. 1, in accordance with example implementations, a downhole tool 150 may be deployed in a wellbore 110 of a well 100 for such purposes as acquiring measurements representing the downhole environment. In accordance with example implementations that are discussed herein, the downhole tool 150 is constructed to acquire measurements for purposes of determining properties of fluids of a geologic structure that is traversed by the wellbore 110. More specifically, in accordance with example implementations, the downhole tool 150 includes an optical spectrometer 154, which is constructed to acquire measurements representing how a given downhole fluid interacts with light for purposes of determining a comprehensive characterization of the fluid at reservoir conditions. As examples, the downhole tool 150 may be used to determine such fluid properties as a hydrocarbon composition, a gas/oil ratio, a carbon dioxide level, and so forth.

In accordance with example implementations, the optical spectrometer 154 may be operated to illuminate a fluid contained in the spectrometer's flow line and apply the principles of spectroscopy for purposes of acquiring information about the fluid. In accordance with some implementations, the downhole tool 150 includes a processing system 152 that processes information acquired by the spectrometer 154 for purposes of performing analysis of the fluid downhole and communicating information uphole about the sampled downhole fluid/reservoir conditions. In this regard, as depicted in FIG. 1, in accordance with some implementations, the downhole tool 150 may include a telemetry interface 156, which communicates data uphole representing the measurements/conditions acquired by the downhole tool 150. In accordance with further example implementations, the processing system 152 may be disposed at Earth surface of the well 100 or completely at another location.

Although example implementations are described herein in which an optical spectrometer is deployed in a well, in accordance with further example implementations, the spectrometer may be used outside of the well and/or for applications that involve analyzing fluids other than well fluids.

In accordance with example implementations, the downhole tool 150 may be deployed downhole using a conveyance mechanism 131, such as a wireline, a coiled tubing string, a slickline, and so forth. Moreover, as depicted in FIG. 1, in accordance with some implementations, the downhole tool 150 may be deployed inside a tubing string 120. Depending on the particular implementation, the tubing string 120 may be a casing string, which lines and supports the wellbore 110. However, in accordance with further example implementations, the tubing string 120 may be a string that is not cased to the wellbore 110 (as depicted in FIG. 1), but rather, the tubing string 120 may be sealed via one or more annular seal devices, such as one or multiple packers 130, as illustrated in FIG. 1.

Spectroscopy is based on the premise that when light shines on a material, the interaction of the light with the material produces a measurable response, which characterizes a property of the material. More specifically, when light having a wavelength $\lambda$ shines directly on the material, the interaction of the light with the material may be defined by a transmittance, (herein called the "$T(\lambda)$"). The $T(\lambda)$ transmittance is the ratio of the intensity of the light (called "I ($\lambda$)" herein) that exits the opposite face of the material to the intensity of the light (called "Io ($\lambda$)" herein) that is incident on the material, as described below:

$$T(\lambda)=I(\lambda)/Io(\lambda). \qquad \text{Eq. 1}$$

Thus, the transmittance $T(\lambda)$ is the ratio of light transmitted through the sample to the light incident on the sample; and as such, the $T(\lambda)$ transmittance has a value of 1.0 when none of the light "disappears." Any light that is not transmitted through the material means that the light is either reflected from, absorbed in, or scattered by the material.

In accordance with example implementations, the downhole tool 150 samples a fluid and uses the spectrometer 154 to measure how much light the fluid absorbs at different wavelengths. Because measuring the absorption directly may be rather difficult, in accordance with example implementations, the downhole tool 150 measures the $T(\lambda)$ transmittance and infers the absorption from the measured $T(\lambda)$ transmittance. In this manner, in the absence of reflections and scattering, absorption is directly related to the $T(\lambda)$ transmittance. If the reflections and scattering, in general, have a uniform effect (i.e., are not dependent on wavelength), then inferring absorption from the $T(\lambda)$ transmittance has a relatively small error.

The $T(\lambda)$ transmittance may be rather inconvenient to use when working with absorption, but classical optics shows that absorption is a logarithmic function of the $T(\lambda)$ transmittance. Furthermore, when the total absorption of a material is the result of several different mechanisms, some of which overlap in some regions of the spectrum, a term called optical density (abbreviated herein as "OD") may be used. The relationship between the $T(\lambda)$ transmittance and OD may be described as follows:

$$OD=\log(T(\lambda)). \qquad \text{Eq. 2}$$

All parts of the spectrometer's light path (i.e., the optical fibres, filters, and so forth) absorb some of the light. To account for this absorption, the spectrometer 154 may be calibrated with a non-absorbing fluid (such as air) in the spectrometer's flow line/measurement region. Measurements that are conducted with on the non-absorbing fluid are referred to herein as the "dry condition," or "dry," measurements; and measurements that are conducted on a liquid fluid are referred to herein as the "wet condition," or "wet," measurements.

Figure 2:
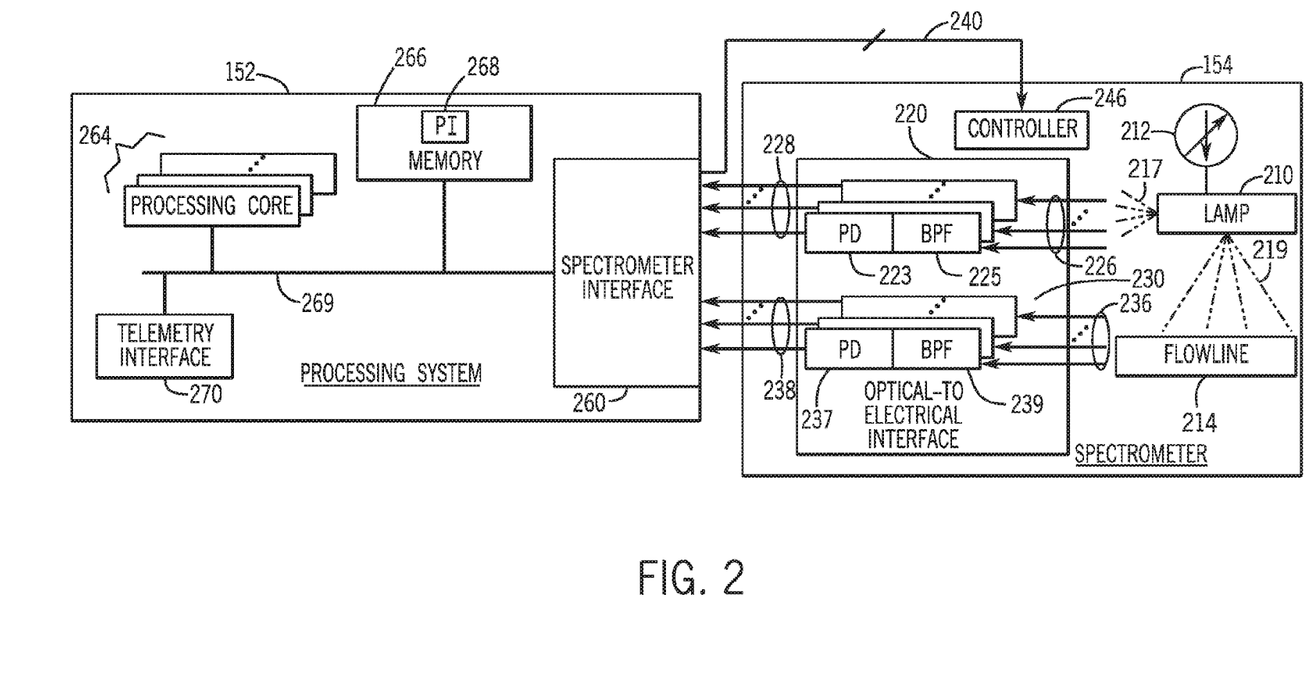
FIG. 2 is a schematic diagram for a fluid analysis tool of FIG. 1 according to an example implementation.

FIG. 2 generally depicts a schematic diagram of the spectrometer 154 and the processing system 152 of the downhole tool 150, in accordance with example implementations. As depicted in FIG. 2, in accordance with example implementations, the spectrometer 154 includes a lamp 210 (a halogen lamp, for example) which produces light that travels along a measurement optical path and a reference optical path. As described further herein, the lamp 210 has an adjustable current (and thus, a corresponding adjustable intensity, or optical output), which is controlled by an adjustable current source 212.

More specifically, light from the lamp 210 illuminates a flow line 214, as depicted by representative illumination 219. The flow line 214 contains either an absorbing fluid (for a wet measurement) or a non-absorbing fluid (for a dry measurement). The light passing through the flow line 214 may be routed into an optical fibre bundle and is routed into an optical fibre distributor (not shown) that separates the light into measurement optical channels 236, where each channel 236 may be associated with a different wavelength. Light 217 from the lamp 210, in accordance with example implementations, is also routed into an optical fibre distributor (not shown) and then distributed by the distributor into reference optical channels 226, where each channel 226 may be associated with a different optical wavelength. In accordance with some implementations, each reference optical channel 226 may be associated with a corresponding set of measurement channels 236. Therefore, depending on which measurement channel 236 is the focus of a linear dynamic range measurement for the optical spectrometer 154, the corresponding reference optical channel 226 may also be selected and used.

The optical spectrometer 154 may include an optical-to-electrical interface 220, which provides electrical signals representing sensed net intensities for each of the channels 226 and 236. In this context, the "net intensity" refers to the difference between the intensity sensed for a given channel when the lamp 210 is on and the intensity sensed for the channel when the lamp 210 is off. In accordance with example implementations, the optical-to-electrical interface 220 includes a bandpass filter 225 and photodetector 223 for each reference optical channel 226 for purposes of providing a corresponding electrical voltage 228 that represents the sensed net intensity of the channel 226. Similarly, in accordance with example implementations, the optical-to-electrical interface 220 may include a bandpass filter 239 and a photodetector 237 for each measurement optical channel 236 for purposes of providing a corresponding electrical voltage 238 that represents the sensed net intensity of the channel 236.

The optical spectrometer 154 therefore provides net intensity measurement voltages 228, which represent the net intensities for the measurement channels 236, and net intensity voltages 238, which represent the net intensities for the reference channels 226.

The spectrometer 154 may have a number of different forms, depending on the particular implementation. For a chopper-motor type spectrometer, the measurement and reference channels share optical paths that have the same filters and detectors. For a reference-type spectrometer, the reference channels share different optical paths from the measurement channels (as depicted in the example implementation of FIG. 2).

As also depicted in FIG. 2, in accordance with example implementations, the measurement 238 and reference 228 voltages may be provided to a spectrometer interface 260 of the downhole tool's processing system 152. The processing system 152 may contain one or multiple processing cores 264 (central processing unit (CPU)-based processing cores, for example), which execute program instructions 268 that are stored in a memory 266 of the processing system 152 for purposes of analysing the measurement and reference voltages, controlling operations of the spectrometer 154, processing the measurements to determine an OD linear dynamic range, and so forth. As an example, FIG. 2 depicts control signals 240 that are communicated from the spectrometer interface 260 to a controller 246 of the spectrometer 154, for purposes of controlling various aspects of the spectrometer 154, such as, for example, controlling the current source 212 to control the intensity of the lamp 210.

Among its other features, in accordance with some implementations, the processing system 152 may contain a telemetry interface 270, which generates data for purposes of communicating with circuitry at the Earth surface. In this regard, in accordance with some implementations, the telemetry interface 270 may be coupled to a telemetry tool 152 (see FIG. 1) of the downhole tool 150 for purposes of communicating data uphole. Moreover, the telemetry tool 156 and telemetry interface 270 of the processing system 156 may be used for purposes of communicating commands to the downhole tool 150 (commands to initiate tests, and so forth), depending on the particular implementation.

The OD is a dimensionless value and represents the amount of optical absorption of a fluid (crude oil, water, gas and so forth) in the spectrometer's flow line 214. The OD for a particular measurement wavelength, or channel (where "i" below represents a channel index), and tool temperature (T) may be described as follows:

$$OD_i(T) = LMSR_{Meas,i} LMSR_{MC,i} TC(T). \quad \text{Eq. 3}$$

In Eq. 3, "LMSR," in general, represents a logarithmic measurement-to-reference ratio; "$LMSR_{Meas,i}$" represents the LMSR ratio for a given channel i for wet condition measurements (i.e., measurements when the liquid fluid is in the flow line 214); "$LMSR_{MC,i}$" represents the LMSR ratio for a given channel i for dry condition measurements (i.e., measurements when the dry fluid is in the flow line 214); and "TC(T)" represents a temperature coefficient to compensate the OD baseline drift due to temperature change.

In general, the LMSR ratio may be described as follows:

$$LMSR = \log_{10} \frac{V_{Meas\,On} - V_{Meas\,Off}}{V_{Ref\,On} - V_{Ref\,Off}}. \quad \text{Eq. 4}$$

In Eq. 4, "$V_{Meas}$" and "$V_{Ref}$" represent the voltages (that represent the net intensities) from the measurement and reference channels, respectively. The "On" and "Off" suffixes of Eq. 4 denote when the lamp 219 is turned on and off, respectively. In accordance with example implementations, the OD values for all channels are calibrated to be zero for the dry condition measurement.

One performance specification for the optical spectrometer 154 may be the dynamic range of OD measurements, which describes the maximum OD measurement capability of the spectrometer 154. The instrument dynamic range is simply the numerical range an instrument can display. Another performance specification for the optical spectrometer 154 may be the "linear dynamic range" of the OD (also referred to as the "OD linear dynamic range," herein), which specifies, for a given acceptable deviation from linearity (as a percentage of absorbance), the minimum and maximum OD values (i.e., the range of OD values that comply with the given acceptable deviation). In accordance with example implementations that are described herein, the "OD linear dynamic range" for the spectrometer 154 may be defined as the OD dynamic range, where OD measurements meet a specified accuracy and linearity.

In accordance with example implementations, the OD linear dynamic range is determined using a fixed reference measurement. In this manner, the reference measurement is a fixed optical attenuation component that does not vary with lamp current. In accordance with example implementations, the OD linear dynamic range for a given wavelength may be determined by determining a reference OD value for the spectrometer 154 and then, determining a range of ODs (including the reference OD), which comply with a specified linearity. More specifically, in accordance with example implementations, maximum ODs (a reference maximum OD and candidate maximum ODs) are calculated using a reference measurement (acquired by the spectrometer 154), which does not vary with the intensity of the lamp 210. A subset of the candidate ODs are then selected based on a specified error between the candidate maximum OD and the reference maximum OD.

More specifically, in accordance with example implementations, the reference measurement may be the measured net intensity of one of the reference channels 226 (see FIG. 2) for a maximum value for the lamp current (i.e., the net intensity measured when the lamp 210 is at its maximum intensity); and the reference maximum OD may be derived from wet and dry condition measurements evaluated at this maximum lamp current. The candidate maximum ODs may be derived from wet and dry measurements acquired using the other lamp currents, with the reference measurement being used in these maximum OD calculations. These candidate maximum ODs may then be compared against the reference maximum OD to determine associated errors with respect to the reference maximum OD. Based on a specified absolute error range, the OD linear dynamic range for the spectrometer may then be determined.

Figure 4:
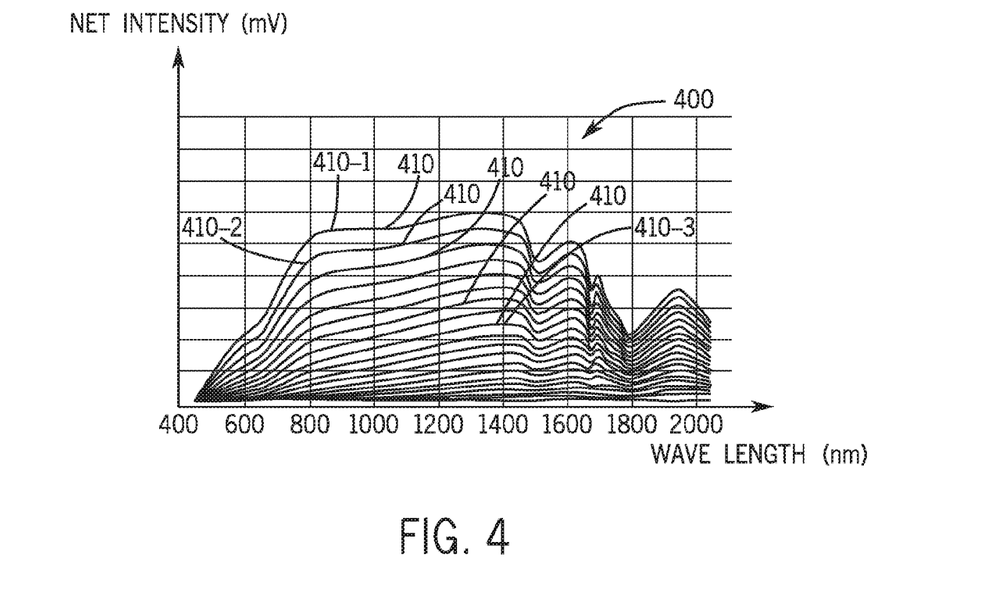
FIG. 4 is an illustration of net intensity spectra measured for a dry flow line condition at different lamp currents of the spectrometer according to an example implementation.

As a more specific example, FIG. 4 illustrates net intensity spectra 400 acquired, or measured, by the optical spectrometer 154 for a dry flow line 214. For these measurements, air, a dry fluid, for example, may be introduced into the optical spectrometer's flow line 214 (FIG. 2), and the controller 246 (FIG. 2) may control the current source 212 so that the optical spectrometer 154 acquires individual spectra 410 for each lamp current value of a predefined range of lamp current values. Thus, for example, spectra 410-1 corresponds to the maximum lamp current value; spectra 410-2 corresponds to the next highest lamp current value (i.e., the maximum lamp intensity); and spectra 410-3 corresponds to a significantly lower lamp current (i.e., a significantly lower lamp intensity). In general, as depicted in FIG. 4, the optical spectrum is shifted to longer wavelengths when the lamp current turns down.

Figure 5:
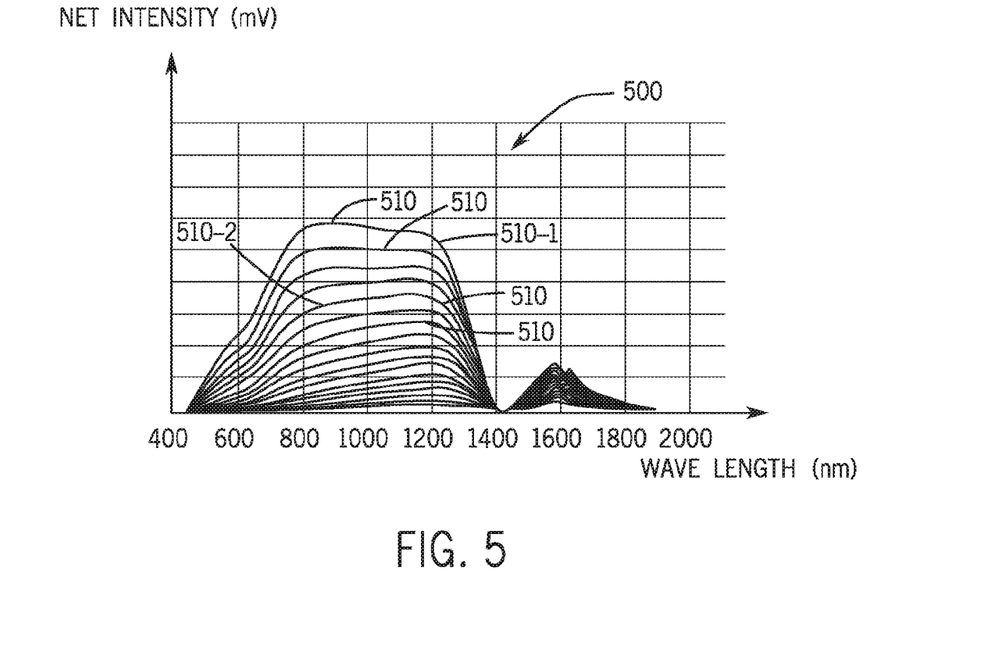
FIG. 5 is an illustration of net intensity spectra measured for a wet flow line condition at different lamp currents for the spectrometer according to an example implementation.

The controller 246 may also control the optical spectrometer 154 to conduct wet condition measurements when a liquid fluid is introduced into the flow line 214, resulting in the spectrometer 154 acquiring net intensity spectra 500 that are depicted in FIG. 5. Referring to FIG. 5, the spectra 500 include individual spectra 510 corresponding to different lamp currents, such as spectra 510-1 corresponding to the maximum lamp current value, spectra 510-2 corresponding to a lower lamp current value, and so forth. As illustrated in FIG. 5, some channels are highly attenuated due to the absorption of the light by the liquid fluid. For example, in FIG. 5, the channel at 1445 nanometers (nm) absorbs a significant amount of light, resulting in a measured net intensity near zero.

In accordance with example implementations, determining the maximum ODs, as well as other aspects described herein pertaining to determining the OD linear dynamic range may be performed by a processor-based system, such as the processing system 152 (FIG. 2), a surface-disposed processing system, a processing system disposed at a remote location, and so forth. For example, one or multiple processing cores 264 of the processing system 152 may executed by program instructions 268 that are stored in a non-transitory memory 266 of the system 152 for purposes of performing calculations to determine the linear dynamic range of the OD. Depending on the particular implementation, the dry and/or wet condition measurements may be performed in or out of the well. Thus, many implementations are contemplated, which are within the scope of the appended claims.

In accordance with example implementations, the reference measurement used for maximum OD calculations is the measurement of the net intensity of one of the reference channels 226 when the lamp current is at its maximum value; and the reference maximum OD is determined based on the spectrometer's wet and dry condition measurements at the maximum lamp current. Moreover, for purposes of determining the other candidate maximum ODs, the lamp current is varied; wet and dry measurements are acquired using these other lamp currents; and the corresponding candidate maximum ODs are calculated based on the wet and dry measurements and the reference measurement.

Figure 6:
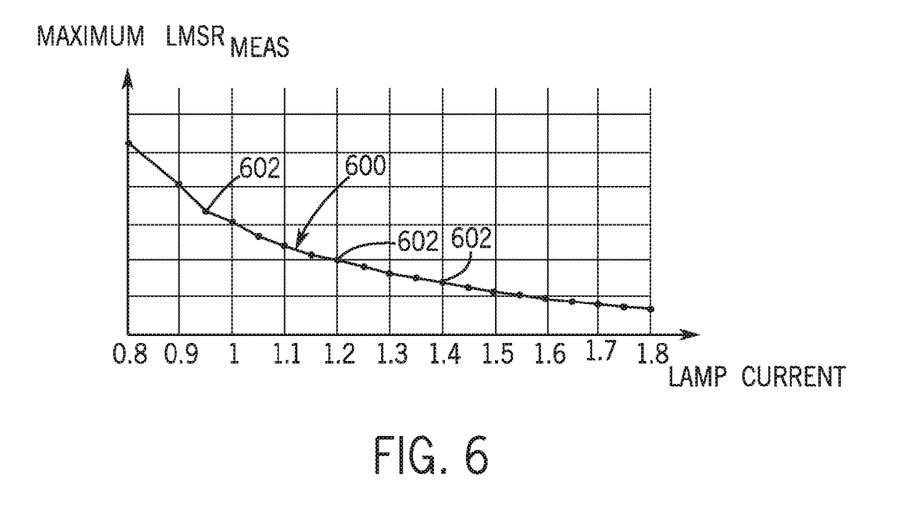
FIG. 6 is an illustration of a maximum attenuation for an optical density versus lamp current for a given wavelength according to an example implementation.

FIG. 6 depicts a maximum attenuation versus lamp current curve 600 for the measurement channel of 1445 nm. In this manner, the maximum attenuation curve 600 contains points, or values 602, which correspond to the maximum LMSR values for different lamp current values for the 1445 nm channel.

Figure 7:
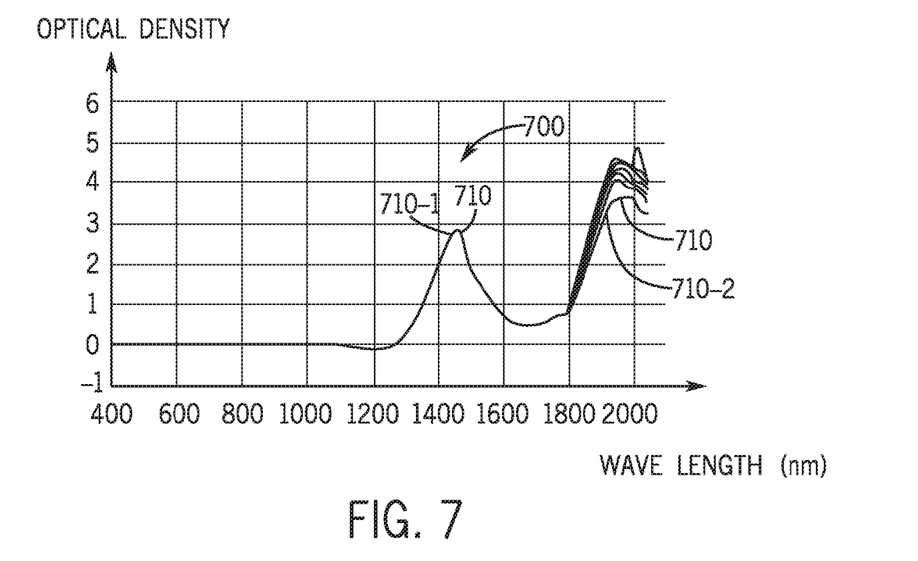
FIG. 7 is an illustration of optical density spectra for different lamp currents according to an example implementation.

The dry LMSR values change with the lamp current. Therefore, the fluid measurement results of FIG. 4 may be calibrated with the measurement results of FIG. 5 (e.g., by subtracting the dry fluid LMSR from the liquid fluid LMSR) to obtain the OD spectra 700 of FIG. 7.

Figure 8:
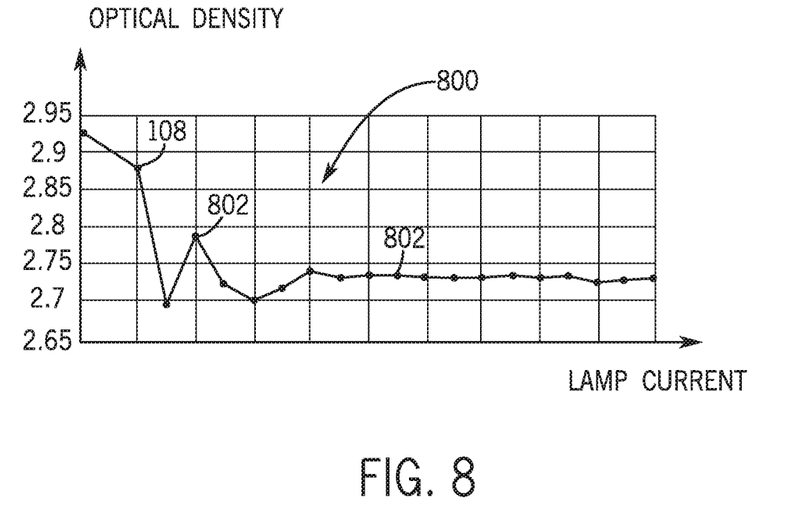
FIG. 8 is an illustration of an optical density versus lamp current for a given wavelength according to an example implementation.

FIG. 8 illustrates an OD 800 versus lamp current for the 1445 nm channel. In this regard, FIG. 8 depicts values 802 of the OD for the 1445 nm channel for different lamp currents. As illustrated in FIG. 8, there are significant OD errors for lower lamp current values.

The OD errors may be calculated by taking the difference between each candidate maximum OD and the reference maximum OD. The resulting subtraction results in a relationship 900 of FIG. 9. As shown, an optical density error 900 may be obtained and may be bounded by a box 910, which defines a specified, or predetermined, maximum error range for the maximum OD. The optical density error 900 may be plotted versus the maximum optical density so that the OD linear dynamic range for the spectrometer 154 is defined by the maximum optical densities that remain inside the box 910.

Figure 9:
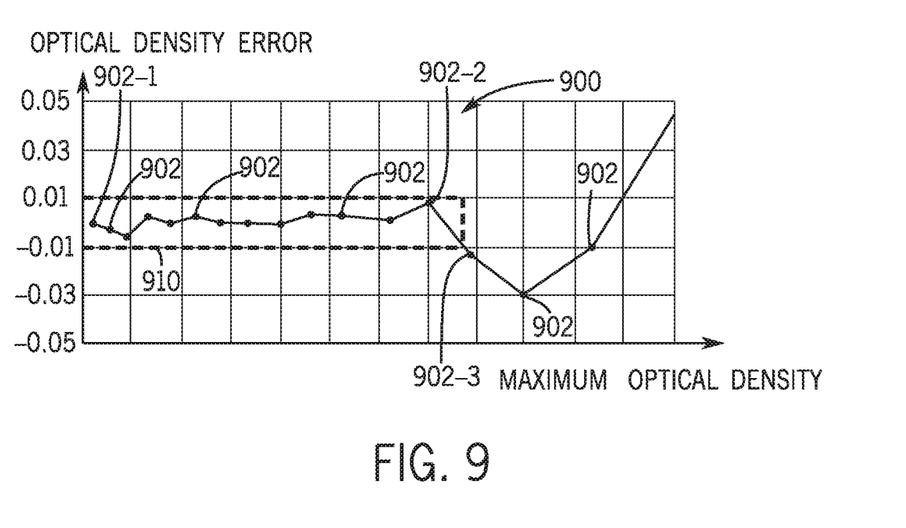
FIG. 9 is a plot of an optical density error versus a maximum optical density illustrating determination of an OD linear dynamic range for an optical spectrometer according to an example implementation.

As depicted in FIG. 9, optical density errors 902 are plotted for various associated candidate maximum optical densities. The reference maximum optical density error 902-1 has an error of zero. The errors 902 within the box 910 range from the error 902-1 associated with the reference maximum optical density to a maximum acceptable error 902-2. Above the maximum optical density associated with the error 902-2, the errors, such as error 902-3, are beyond the predetermined error range. Thus, box 910 defines the OD linear dynamic range for the spectrometer 154.

Figure 3:
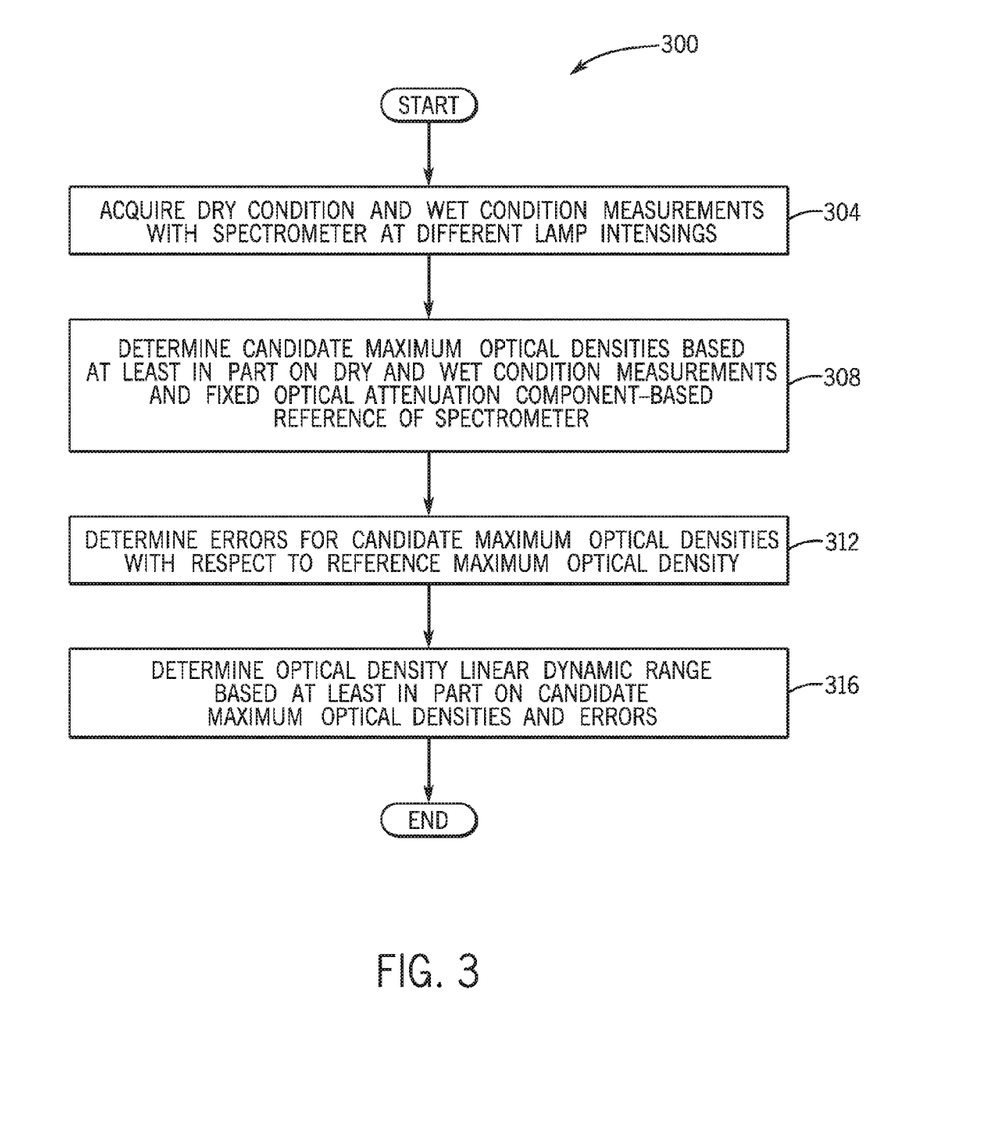
FIGS. 3 and 10 are flow diagrams depicting techniques to determine an optical density (OD) linear dynamic range of an optical spectrometer according to example implementations.

Referring to FIG. 3, thus, in accordance with example implementations, a technique 300 includes acquiring (block 304) dry condition and wet condition measurements with a spectrometer for different lamp current intensities for a given measurement wavelength. The technique 300 includes determining (block 308) candidate maximum optical densities based at least in part on the dry and wet condition measurements and a fixed, optical attenuation-based reference. The technique 300 includes determining (block 312) errors for the candidate maximum optical densities with respect to a reference maximum optical density. An optical density linear dynamic range may then be determined, pursuant to block 316, based at least in part on the candidate maximum optical densities and the errors.

Figure 10:
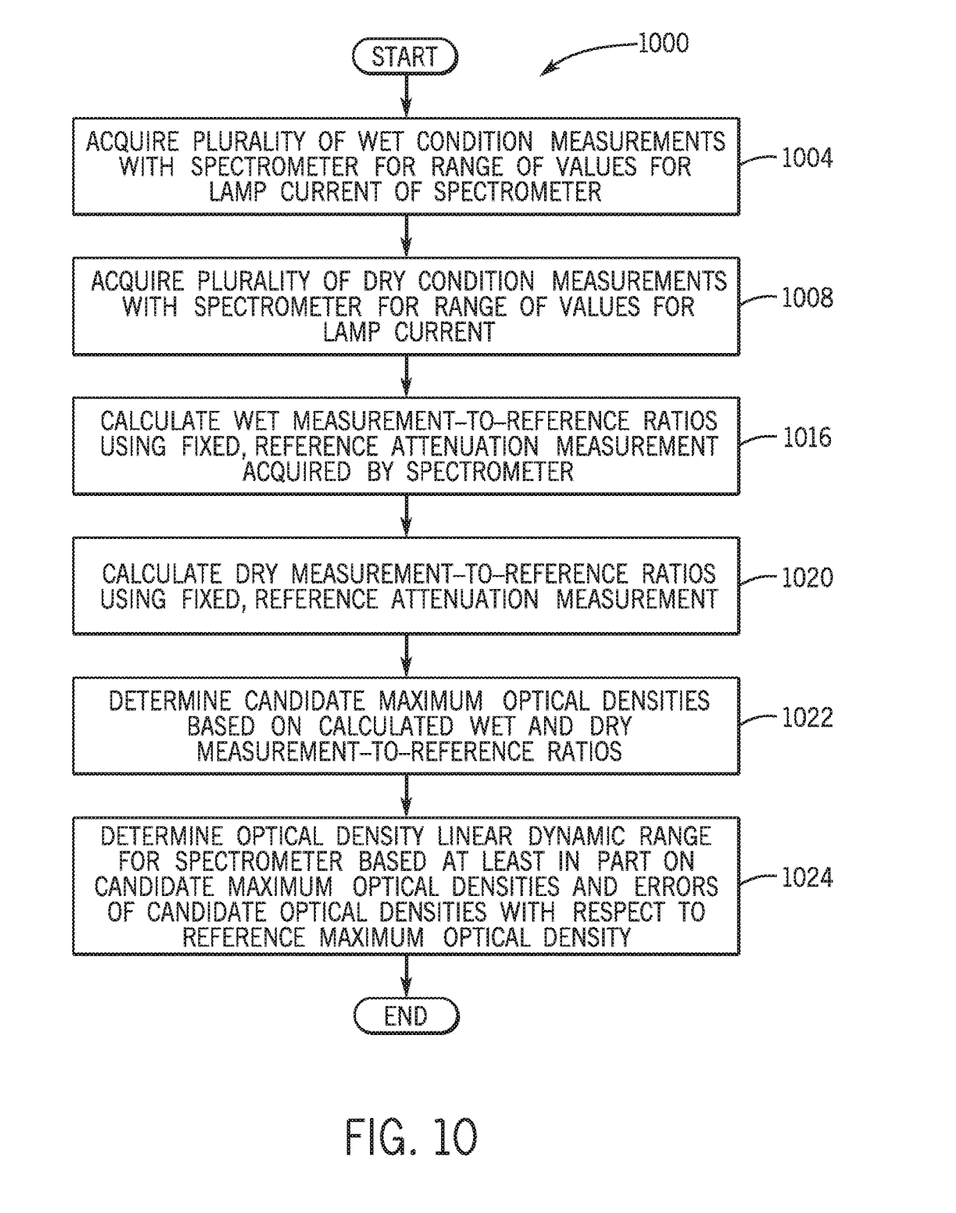

More specifically, referring to FIG. 10, in accordance with example implementations, a technique 1000 may be used to determine an OD linear dynamic range for a spectrometer. The technique 1000 includes acquiring (block 1004) a plurality of wet condition measurements with the spectrometer for a range of values for a lamp current of the spectrometer, and acquiring (block 1008) a plurality of dry condition measurements with the spectrometer for the lamp current values. The technique 1000 includes calculating (block 1016) wet measurement-to-reference ratios using a fixed, reference attenuation measurement acquired by the spectrometer; and calculating (block 1020) dry measurement-to-reference ratios using the fixed, reference attenuation measurement. Candidate maximum optical densities for the lamp currents may then be determined based on the wet and dry measurement-to-reference ratios, pursuant to block 1022. The technique 1000 includes determining (block 1024) an optical density linear dynamic range for the spectrometer based at least in part on the candidate maximum optical densities and errors of the candidate maximum optical densities with respect to a reference maximum optical density.

The techniques and systems that are described herein assume the non-existence of stray light. Stray light may be defined as the unwanted light contribution (or cross-talk) from other wavelengths outside of the measurement channel (the measurement wavelength). This stray light exists when the blocking level of the optical bandpass filter (one of the bandpass filters 225 or 239 of FIG. 2, for example) is not sufficiently high enough, as compared to the system's OD dynamic range. The stray light effect becomes more pronounced when the signal at the measurement channel is very weak.

In accordance with example implementations, for purposes of determining whether there is any stray light effect, the performances of the channel bandpass filters 225 and 239 (see FIG. 2) may be tested based on the OD dynamic range of the system. In accordance with example implementations, the channel isolation, or OD blocking level, of an optical filter should be much higher than the OD dynamic range of the tool to ensure that there is no stray light effect arising from that filter.

As a more specific example, in accordance with some implementations, the OD blocking level for the bandpass filters may be defined as an OD greater than four. The filters may be tested for other blocking levels, in accordance with further implementations.

Other implementations are contemplated which are within the scope of the appended claims. For example, in accordance with some implementations, for purposes of determining an OD linear dynamic range for multiple measurement wavelengths, or channels, liquids that attenuate significant energy at these wavelengths, may be selectively introduced into the flow line 214 for the wet condition measurements. In accordance with some implementations, the spectrometer 154 may contain an optical filter with a fixed attenuation for purposes of selecting another peak channel for the OD linear dynamic range determination. The techniques that are described herein may be applied to other types of spectrometers by introducing the appropriate fixed attenuation component. Thus, many implementations are contemplated, which are within the scope of the appended claims.

In accordance with further example implementations, the techniques that are described herein may be used for purposes of determining the linear dynamic range for a spectrometer other than a spectrometer that is used downhole in a well. Moreover, the measurements that are described herein may be conducted outside of the well.

While the present techniques have been described with respect to a number of embodiments, it will be appreciated that numerous modifications and variations may be applicable therefrom. It is intended that the appended claims cover all such modifications and variations as fall within the scope of the present techniques.

What is claimed is:

1. A method comprising:
   acquiring dry condition and wet condition measurements using an optical spectrometer for a plurality of lamp currents;
   determining candidate maximum optical densities as a function of lamp intensities of the spectrometer based at least in part on a reference measurement acquired by the spectrometer, the reference measurement not varying with respect to the lamp intensities; and
   determining an optical density linear dynamic range based at least in part on the candidate maximum optical densities.

2. The method of claim 1, further comprising:
   measuring a net intensity of a reference channel of the optical spectrometer for a predetermined lamp current of a plurality of lamp currents; and
   using the measured net intensity as the reference measurement.

3. The method of claim 2, wherein determining the candidate maximum optical densities comprises:
   for each lamp current value of the plurality of lamp current values, determining the maximum optical density based on net intensities observed for a measurement channel of the optical spectrometer for a dry flow line and for a liquid filled flow line of the optical spectrometer and the measured net intensity of the reference channel.

4. The method of claim 2, wherein the predetermined lamp current comprises a maximum value of the plurality of lamp current values.

5. The method of claim 1, wherein determining the optical density linear dynamic range comprises:
   determining errors between the candidate maximum optical densities and a reference maximum optical density.

6. The method of claim 1, wherein determining the optical density linear dynamic range further comprises:
   determining a range of the candidate maximum optical densities that have errors within a predetermined error range.

7. A method comprising:
   acquiring a plurality of wet condition measurements using an optical spectrometer for a range of values for a lamp current of the spectrometer;
   acquiring a plurality of dry condition measurements using the spectrometer for the range of values for the lamp current;
   determining first measurement-to-reference ratios for the wet condition measurements;
   determining second measurement-to-reference ratios for the dry condition measurements;
   acquiring a fixed reference attenuation measurement using the spectrometer;
   determining candidate maximum optical densities for the spectrometer for the range of values for the lamp current based at least in part on the first measurement-to-reference ratios, the second measurement-to-reference ratios and the candidate maximum optical densities; and
   determining a linear dynamic range of optical density measured by the spectrometer based at least in part on errors determined based at least in part on the determined maximum optical densities.

8. The method of claim 7, wherein acquiring the plurality of wet condition measurements comprises acquiring net intensities associated with measurement channels of the spectrometer in response to a liquid fluid being disposed in a flow line of the spectrometer.

9. The method of claim 7, wherein acquiring the plurality of dry condition measurements comprises acquiring net intensities associated with measurement channels of the spectrometer in response to a dry fluid being disposed in a flow line of the optical spectrometer.

10. The method of claim 7, wherein calculating at least one of the candidate maximum optical densities comprises:
    determining a first attenuation based on a ratio of the wet measurement corresponding to a given lamp current to the reference measurement;
    determining a second attenuation based on a ratio of the dry measurement corresponding to the given lamp current to the reference measurement; and
    subtracting the second attenuation from the first attenuation.

11. The method of claim 7, wherein determining the reference measurement comprises measuring a net intensity of a reference channel of the spectrometer for a predetermined value of the lamp current values.

12. The method of claim 11, wherein the predetermined value comprises the maximum lamp current value.

13. An apparatus, comprising:
    an interface to receive data representing net intensities measured by an optical spectrometer representing wet condition and dry condition measurements acquired by an optical spectrometer for a plurality of lamp currents; and a processor to process the data to:
  determine maximum optical densities for the plurality of lamp currents based at least in part on a reference measurement acquired by the spectrometer, the reference measurement not varying with respect to the lamp current; and
  determine an optical density linear dynamic range for the spectrometer based at least in part on the candidate maximum optical densities and a reference maximum optical density.

14. The apparatus of claim 13, wherein the optical spectrometer comprises a reference channel, and the processor calculates the reference measurement based on a net intensity acquired using the reference channel.

15. The apparatus of claim 13, wherein the processor calibrates the maximum optical density to a predetermined value for a given lamp current value of the plurality of lamp current values.

16. The apparatus of claim 13, wherein the processor, for each lamp current value of the plurality of lamp current values, determines an attenuation ratio based on a net intensity observed for a measurement channel of the spectrometer for each lamp current value to a net intensity associated with the reference measurement.

17. The apparatus of claim 13, wherein the reference measurement is associated with a measurement acquired using the maximum lamp current.

18. The apparatus of claim 17, wherein the processor:
  for each lamp current value of the plurality of lamp current values, determines the maximum optical density based on net intensities observed for a dry flow line and for a liquid filled flow line, and the reference measurement.

19. The apparatus of claim 18, wherein the reference measurement corresponds to an observed intensity of reference channel of the spectrometer for a maximum value of the plurality of lamp current values.

20. The apparatus of claim 13, wherein the processor determines errors between the candidate maximum optical densities and the reference maximum optical density.

* * * * *